(12) United States Patent
Lombardi et al.

(10) Patent No.: US 6,203,568 B1
(45) Date of Patent: Mar. 20, 2001

(54) ENDOLUMINAL PROSTHESES HAVING POSITION INDICATING MARKERS

(75) Inventors: Sylvie Lombardi, Palo Alto; Steven W. Kim; Darin C. Gittings, both of Sunnyvale; Michael A. Evans, Palo Alto; Jay A. Lenker, Los Altos Hills; Allan R. Will, Atherton, all of CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/122,337

(22) Filed: Jul. 24, 1998

Related U.S. Application Data

(62) Division of application No. 08/628,797, filed on Apr. 5, 1996, now Pat. No. 5,824,042.

(51) Int. Cl.⁷ ............................. A61F 2/06; A61M 25/098
(52) U.S. Cl. ...................... 623/1.13; 623/1.16; 623/1.23; 623/1.35; 600/36; 606/194
(58) Field of Search .................................... 623/1.13, 1.16, 623/1.23, 1.35; 600/36; 606/194

(56) References Cited

U.S. PATENT DOCUMENTS

| | | |
|---|---|---|
| 4,202,349 | 5/1980 | Jones . |
| 4,617,932 | 10/1986 | Kornberg .............................. 128/334 |
| 5,151,105 | 9/1992 | Kwan-Gett ............................... 623/1 |
| 5,209,730 | 5/1993 | Sullivan ................................. 604/96 |
| 5,275,622 | 1/1994 | Lazarus et al. ........................... 623/1 |
| 5,366,504 | 11/1994 | Anderson et al. ...................... 623/11 |
| 5,419,324 | 5/1995 | Dillow ............................... 128/653.1 |
| 5,464,438 | 11/1995 | Menaker ................................. 623/1 |
| 5,476,508 | 12/1995 | Amstrup ................................. 623/1 |
| 5,484,418 | 1/1996 | Quiachon et al. .................... 604/167 |
| 5,489,295 | 2/1996 | Piplani et al. ........................... 623/1 |
| 5,562,726 | 10/1996 | Chuter .................................... 623/1 |
| 5,562,728 | 10/1996 | Lazarus et al. .......................... 623/1 |
| 5,662,675 | 9/1997 | Polanskyj Stockert et al. .... 606/194 |
| 5,718,724 | 2/1998 | Goicoechea et al. ..................... 623/1 |

FOREIGN PATENT DOCUMENTS

| | | | |
|---|---|---|---|
| 0 146 699 | 7/1985 | (EP) . | |
| 0 480 667 | 4/1992 | (EP) . | |
| 0 508 473 | 10/1992 | (EP) . | |
| 0 649 637 A1 | 7/1995 | (EP) | ............................... A61F/2/06 |
| 0 669 114 | 8/1995 | (EP) . | |
| 0 679 372 A2 | 11/1995 | (EP) | ............................. A61B/19/00 |
| 0 680- 734 A2 | 11/1995 | (EP) | ................................ A61F/2/06 |
| 0 684 022 A2 | 11/1995 | (EP) | ................................ A61F/2/06 |
| 0 686 379 | 12/1995 | (EP) . | |
| 0 699 423 A2 | 3/1996 | (EP) | ................................ A61F/2/06 |
| 0 709 068 | 5/1996 | (EP) | ................................ A61F/2/06 |
| WO 90/15582 | 12/1990 | (WO) | ................................ A61F/2/06 |
| WO 91/155254 | 10/1991 | (WO) | ............................ A61M/5/00 |
| WO 95/03010 | 2/1995 | (WO) | ................................ A61F/2/06 |
| WO 95/08966 | 4/1995 | (WO) | ................................ A61F/2/06 |
| WO 95/21592 | 8/1995 | (WO) | ................................ A61F/2/06 |

*Primary Examiner*—Vincent Millin
*Assistant Examiner*—Choon P. Koh
(74) *Attorney, Agent, or Firm*—Sterne, Kessler, Goldstein & Fox PLLC

(57) ABSTRACT

The present invention provides an endoluminal prosthesis for deployment in a body lumen of a patient body, the prosthesis comprising a tubular fabric liner and a radially expandable frame supporting the liner. A plurality of imagable bodies are attached to the liner, the imagable bodies providing a sharp contrast so as to define a pattern which indicates the prosthesis position when the prosthesis is imaged within the patient body. Preferably, each imagable body comprises a plate having first and second opposed major surfaces and a passage therebetween to facilitate stitching the imagable body to the liner. Advantageously, the imagable bodies can be aligned with the openings of a perforate frame structure so that at least some of the imagable bodies are visible through associated openings, but need not actually be attached to the frame directly. Such imagable bodies are clearly visible when the prosthesis is deployed, and can also be sized to produce distinct images even when the frame is compressed within a delivery catheter, but will not interfere with the radial expansion of the frame during deployment.

27 Claims, 14 Drawing Sheets

ENDOLUMINAL PROSTHESES HAVING POSITION INDICATING MARKERS

This application is a division of and claims the benefit of priority from U.S. application Ser. No. 08/628,797, filed Apr. 5, 1996, now U.S. Pat. No. 5,824,042, the full disclosure of which is incorporated herein by reference.

BACKGROUND OF THE INVENTION

1. Field of the Invention

The present invention relates generally to tubular prostheses, such as grafts, stents, stent-grafts, and the like. More particularly, the present invention provides endoluminal prostheses having discrete position indicating elements which facilitate orienting and deploying the prostheses within body lumens, particularly within branching blood vessels for the treatment of abdominal and other aneurysms.

Vascular aneurysms are the result of abnormal dilation of a blood vessel, usually resulting from disease and/or genetic predisposition, which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending into one or both of the iliac arteries.

Aortic aneurysms are most commonly treated in open surgical procedures, where the diseased vessel segment is bypassed and repaired with an artificial vascular graft. While considered to be an effective surgical technique, particularly considering the alternative of a usually fatal ruptured abdominal aortic aneurysm, conventional vascular graft surgery suffers from a number of disadvantages. The surgical procedure is complex and requires experienced surgeons and well equipped surgical facilities. Even with the best surgeons and equipment, however, patients being treated frequently are elderly and weakened from cardiovascular and other diseases, reducing the number of eligible patients. Even for eligible patients prior to rupture, conventional aneurysm repair has a relatively high morality rate, usually from 2% to 10%. Morbidity related to the conventional surgery includes myocardial infarction, renal failure, impotence, paralysis, and other conditions. Additionally, even with successful surgery, recovery takes several weeks, and often requires a lengthy hospital stay.

In order to overcome some or all of these drawbacks, endovascular prosthesis placement for the treatment of aneurysms has been proposed. Although very promising, many of the proposed methods and apparatus suffer from undesirable limitations. In particular, proper positioning of an endovascular prosthesis within the vascular system can be problematic.

Accurately positioning and orienting endoluminal prostheses is critical to the efficacy of endovascular aneurysm therapies. These tubular prostheses are generally introduced into the vascular system within a catheter and in a radially compressed configuration, typically being maneuvered into position under fluoroscopy. The positioned prosthesis will radially expand, preferably engaging and sealing against the endolithium of the healthy vessel wall both upstream and downstream of the weakened, distended aneurysm. The prosthesis may expand resiliently when released from the catheter, or may be mechanically expanded, typically using a balloon catheter. In either case, the prosthesis will preferably span the entire aneurysm to prevent pressure from acting on the weakened lumenal wall, and to prevent leakage through any rupture of the aneurysm. To provide these advantages, the prosthesis must be axial positioned accurately across the aneurysm so as to isolate it from the blood flow through the prosthetic lumen.

Proper radial orientation of endoluminal prostheses is also important, particularly when deploying branching and asymmetric prostheses within the tortuous vascular system. If the branches of branching prostheses are not oriented toward their respective branching body lumens, the surrounding body lumen may be distended to adapt to the misaligned prosthesis, or the prosthetic lumen may be distorted or even closed entirely. For example, if the trunk of a bifurcated prosthesis is deployed with a branch oriented 90° from the iliac arteries (i.e., angling dorsally rather than laterally), the prosthetic branch lumen may fold or kink, and will have to at least bend at a sharp angle to enter the laterally oriented iliac. In fact, as branching prostheses are often assembled in situ, it may not be possible to introduce the branch prosthesis into such a misaligned branch port. As recapture or repositioning of expanded endoluminal prostheses is often problematic, it may even be necessary to resort to an emergency invasive procedure to remedy such misalignment.

Tubular endovascular prostheses are often formed as stent-grafts having a flexible tubular liner or "graft" which is supported by a perforate tubular frame or "stent". The frame perforations define radially expandable structures, while the frame often include metals which are, to some extent, visible under fluoroscopy.

To facilitate positioning of endovascular prostheses, it has previously been proposed to coil gold or platinum wires around an element of the perforate frame structure to enhance the visibility of the prosthesis under fluoroscopy. Similarly, it has been suggested that a tube be crimped over an element of the frame. Unfortunately, affixing such structures to the frame may limit or interfere with the radial compressibility of the prosthesis. It can also be difficult to identify the portion of the frame having an enhanced image against the backdrop of the frame itself, and to orient the prosthesis properly based on one or more enhanced frame arms.

Alternatively, it has been suggested to affix radiopaque lines or image markers to bifurcated grafts in the form of fine wire or chain, either woven into the cloth or applied after weaving, or as an inert paint or plastic. However, the liners of endoluminal prostheses must remain highly flexible, typically being folded when the prosthesis is compressed and unfolding during deployment. Wires, chains, or paints which are sufficiently flexible will generally provide only limited-contrast images when the graft is supported by the obscuring frame, and may become detached from the prosthesis once deployed in the body lumen, with potentially catastrophic consequences. Moreover, imaging of such thin, flexible, low-contrast markers is particularly difficult when the prosthesis is in the high density, radially compressed configuration and disposed within a catheter, as is generally required for intravascular maneuvering.

For these reasons, it would be desirable to provide improved endoluminal prostheses and methods for their use. It would be particularly desirable to provide endoluminal prostheses having high-contrast orientation indicating imaging markers which do not interfere with radial compression or expansion, and which are securely and reliably attached to the prosthesis. It would further be desirable if such markers could clearly indicate both the position and orientation of the prosthesis, ideally while the prosthesis remains compressed in the delivery catheter, but without substantially increasing the size of the delivery system.

2. Description of the Background Art

Co-pending U.S. patent application Ser. No. 08/538,706, filed Oct. 3, 1995, the full disclosure of which is hereby incorporated by reference, describes modular prostheses and prosthetic construction methods. Provisional Application Serial No. 60/008,254, filed Dec. 1, 1995, also incorporated herein by reference, describes bifurcated modular prosthetic structures and in situ methods for their assembly.

Published PCT patent application WO 95/21,592 describes a bifurcated endoluminal prosthesis including a bifurcated stent and a second stent. One or more X-ray opaque coils or tubes may de disposed over an arm of the stent structure so that the stents can be aligned and engaged in situ under X-ray monitoring. U.S. Pat. No. 5,387,235 describes a bifurcated graft having radiopaque lines and markers formed of fine wire or chains of inert metal, or of an inert paint or plastic.

SUMMARY OF THE INVENTION

In a first aspect, the present invention provides a tubular graft comprising a polyester fabric and a radiopaque marker disposed on the graft. The marker has been applied to the graft as a compound comprising radiopaque particles, a polyester matrix for affixing the radiopaque particles on the graft, and a polyester solvent. Preferably, a protective overcoat is applied over the marker to prevent the compound from detaching from the graft when the graft flexes during deployment or from physiological movement. Ideally, a precoat is applied before the compound, and the radiopaque particles comprise tantalum particles having an average diameter of between about 1 and 5 microns.

In a preferred aspect, the present invention provides an endoluminal prosthesis for deployment in a body lumen of a patient body, the prosthesis comprising a tubular fabric liner and a radially expandable frame supporting the liner. A plurality of imagable bodies are attached to the liner, the imagable bodies providing a sharp contrast so as to define a pattern which indicates the prosthesis position when the prosthesis is imaged within the patient body. Preferably, each imagable body comprises a plate having first and second opposed major surfaces and a passage therebetween to facilitate stitching the plate to the liner. Advantageously, the imagable bodies can be aligned with the openings of a perforate frame structure so that at least some of the imagable bodies are visible through associated openings, and need not actually be attached to the frame directly. Such imagable bodies are clearly visible when the prosthesis is deployed, and can also be sized to produce distinct images even when the frame is compressed within a delivery catheter, but should not interfere with the radial expansion of the frame during deployment. The imagable bodies optionally comprise a radiopaque material, or may alternatively produce enhanced ultrasound images. Preferably, the frame and the imagable bodies will have a similar electromotive force (EMF) to avoid corrosion.

In another aspect, the present invention provides an endoluminal prosthesis for deployment in a body lumen of a patient body, the prosthesis comprising a tubular fabric liner and a radially expandable frame supporting the liner. A plurality of radiopaque marker elements, each defining a passage therethrough, are stitched to the liner through the passage. The marker elements indicate a position of the prosthesis when the prosthesis is radiographically imaged within the body lumen. In some embodiments, the marker elements comprise plates. Alternatively, the marker elements comprise wires having a plurality of loops which define the passages.

In yet another aspect, the present invention provides an endoluminal prosthesis for deployment in a body lumen of a patient body, the prosthesis comprising a radially expandable tubular body defining a centerline and a plurality of radiopaque marker elements disposed on the body. The marker elements define a pattern when the prosthesis is imaged within the patient body, the pattern including a gate disposed adjacent to a distal or proximal port. The gate comprises radially separated marker elements on opposed sides of the centerline when the prosthesis is properly oriented to facilitate deployment of a secondary prosthetic module within the adjacent port of the prosthesis. Optionally, the pattern may include two axially separated gates which define an allowable prosthetic overlap region therebetween. As the marker elements which define these gates are offset on opposite sides of the centerline, they remain highly visible when the delivery catheter containing the secondary prosthetic module is being positioned within the port.

In yet another aspect, the present invention provides an endoluminal body lumen marker for use in positioning a later deployed endoluminal prosthesis in a body lumen. The lumen marker comprises a body which produces a sharp contrast when imaged within the lumen, and a support structure which maintains a position of the lumen marker within the body lumen until the prosthesis is positioned and deployed across the lumen marker. In some embodiments, the body comprises a radiopaque button, and the support structure comprises a barbed protrusion for attaching the imagable body to the lumenal wall. Alternatively, the support structure comprises a radially expandable radiopaque band, preferably a helical coil, which engages the surrounding body lumen and which marks an axial target location for an end of the prosthesis.

In yet another aspect, the present invention provides an endoluminal stent-graft comprising a tubular liner having a lumen which defines an axis and a perforate tubular frame supporting the liner. The frame has a plurality of integral marker elements formed by local variations in the perforations, the integral marker elements defining a pattern which indicates a position of the prosthesis when the prosthesis is imaged within the body lumen. Generally, the frame comprises a radiopaque material, and the marker elements comprise portions that are wider than the adjacent expandable frame arms to provide an enhanced radiographic contrast.

The present invention further provides a method for fabricating a position indicating endoluminal prosthesis, the method comprising providing a tubular graft comprising a polyester fabric and applying a compound to the graft, the compound comprising a polyester matrix, radiopaque particles, and a polyester solvent so that the polyester matrix adheres to the polyester fabric and permanently affixes the radiopaque particles to the graft.

In another aspect, the present invention provides a method for fabricating a position indicating endoluminal prosthesis for use in a body lumen of a patient body. The method comprises affixing a radially expandable frame to a tubular liner so that the frame supports the liner, and attaching a plurality of marker elements to the liner so that the elements define a pattern. The marker elements are capable of producing a sharp contrast when imaged so that the pattern indicates a position of the prosthesis when the prosthesis is imaged within the patient body. Preferably, the attaching step comprises stitching through at least one opening in each marker element.

In yet another aspect, the present invention provides a method for assembling an endoluminal prosthesis at a target location of a body lumen. The method comprises introducing a first tubular endoluminal prosthetic module into the body lumen and positioning the first module adjacent to the target location. The first module is radially expanded to deploy the module adjacent to the target location, the expanded first module having first and second marker elements disposed adjacent to a port. A second tubular prosthetic module is introducing into the body lumen and positioned within the port of the first module by imaging the first module and axially advancing the second module between the first and second marker elements.

In yet another aspect, the present invention provides a method for positioning a tubular endoluminal prosthesis at a target location of a body lumen. The method comprises introducing a guidewire through the body lumen and advancing the guidewire beyond the target location, and advancing the prosthesis over the guidewire so that the guidewire passes through a lumen of the prosthesis. The prosthesis is radially oriented by imaging the prosthesis within the body lumen and aligning an image of a marker element of the prosthesis with an image of the guidewire.

In yet another aspect, the present invention provides a method for positioning a tubular endoluminal prosthesis at a target location of a body lumen, the method comprising introducing the prosthesis into the body lumen and positioning the prosthesis adjacent to the target location. The prosthesis is radially oriented by imaging the prosthesis within the body lumen and aligning an image of a first marker element of the prosthesis with an image of a second marker element of the prosthesis, wherein the first and second marker elements are axially offset from each other.

In yet another aspect, the present invention provides a method for verifying the radial orientation of a port of a branching tubular endoluminal prosthesis within a body lumen, the method comprising introducing the prosthesis into the body lumen and radially orienting the prosthesis. An end of the prosthesis which is separated from the port is deployed by axially withdrawing a surrounding sheath and allowing the prosthesis end to expand. At least one port orientation indicating marker element disposed on the expanded end of the prosthesis can then be imaged while the prosthesis adjacent the port remains in a compressed state, thereby clearly showing the radial orientation of the port while recompression of the prosthesis is still relatively easy.

In yet another aspect, the present invention provides a method for deploying an endoluminal prosthesis, the method comprising introducing and deploying a marker element in a body lumen so as to mark a target location. The prosthesis is introduced into the body lumen and aligned with the marker element. These marker elements, which may comprise marker bands or barbed imagable bodies, are particularly useful in follow-up procedures to monitor migration of the prosthesis or changes in aneurysms or other disease conditions, which will often appear as changes in the relative positions of the marker element and the prosthesis.

In a final aspect, the present invention provides an endoluminal prosthesis comprising a high-strength frame material and a high-contrast image marker material. To avoid electrolytic corrosion of the prosthesis, the electromotive force characteristics of the frame and marker element materials are substantially similar. Preferably, the frame material comprises a shape memory alloy such as Nitinol™, while the marker element material comprises tantalum.

DESCRIPTION OF THE SPECIFIC EMBODIMENTS

The present invention provides radially expansible tubular prostheses, particularly grafts, stents, and stent-grafts, which generally include discrete, liner supported marker elements that provide a high-contrast image when viewed under fluoroscopy, ultrasound, or some other surgical imaging modality, so as to facilitate the proper positioning of the prosthesis within a body lumen. The prostheses of the present invention are suitable for a wide variety of therapeutic uses, including stenting of the ureter, urethra, trachea, branchi, esophagus, biliary tract, and the like. The present devices and methods will also be useful for the creating of temporary or long term lumens, such as the formation of fistulas.

The prosthetic structures of the present invention will find their most immediate use as endovascular prostheses for the treatment of diseases of the vasculature, particularly aneurysms, stenoses, and the like, and are especially well suited for therapies to treat abdominal aortic aneurysms adjacent the aortal/iliac junction. These prostheses will generally be radially expansible from a narrow diameter configuration to facilitate introduction into the body lumen, typically during surgical cutdown or percutaneous introduction procedures.

The prosthetic structures described hereinbelow will find use in axially uniform cylindrical prostheses, in preassembled bifurcated prostheses, and as prosthetic modules which are suitable for selective assembly either prior to deployment, or in situ. Such selective assembly of prosthetic modules to form a customized endoluminal prosthesis is more fully described in co-pending U.S. patent application Ser. Nos. 60/008,254 and 08/538,706 the full disclosures of which have previously been incorporated herein by reference.

Figure 1:
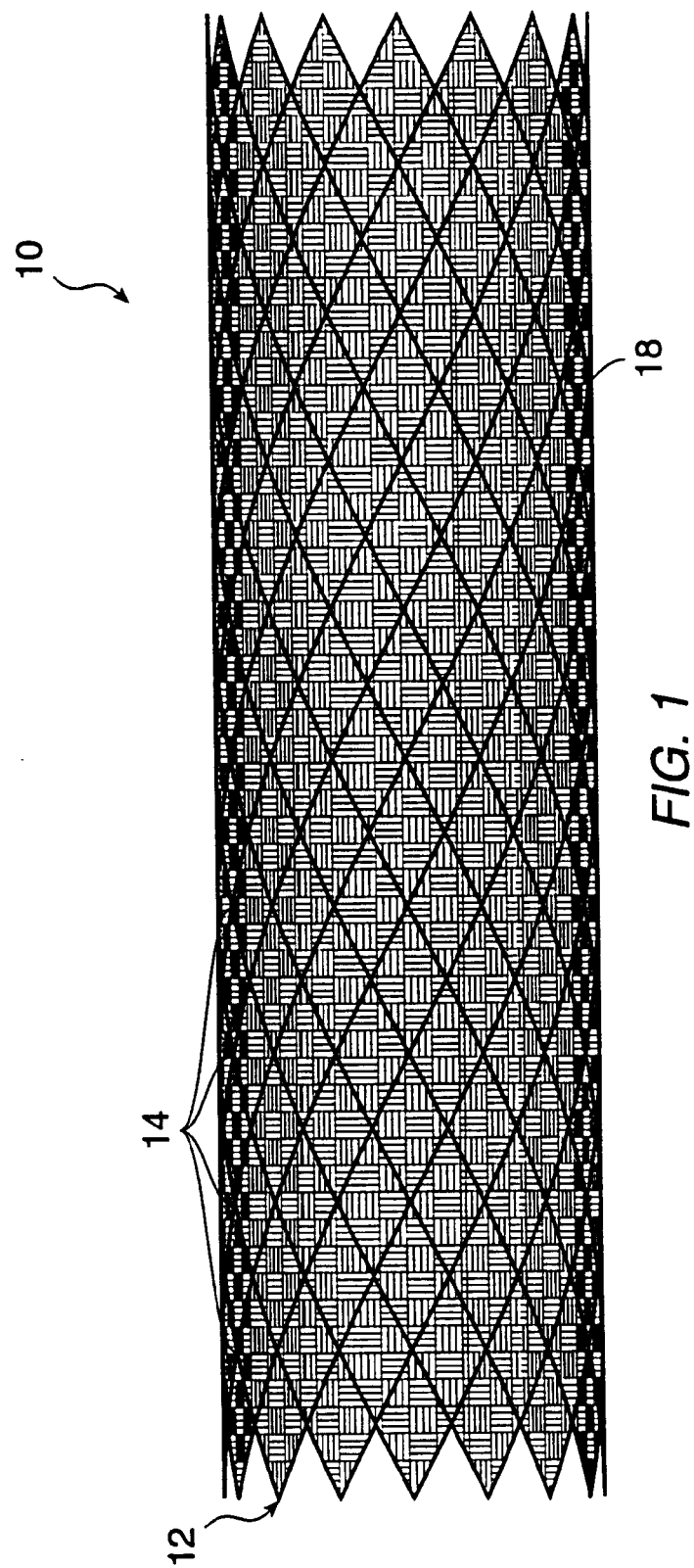
FIG. 1 is a side view of an exemplary cylindrical vascular stent-graft having axially constant characteristics.

An exemplary cylindrical graft structure 10 is illustrated in FIG. 1. Prostheses 10 comprises a perforate tubular frame 12 which includes a plurality of independent (non-connected) ring frames 14. The tubular frame 12 supports an inner liner 18. Optionally, an outer liner is disposed over the ring frames, either inside of inner liner 18, or in combination therewith.

To secure ring frames 14 in place, and to secure the liner to the perforate tubular frame 12, the liner is typically sutured to the frame. A wide variety of alternative liner/frame attachment mechanisms are available, including adhesive bonding, heat welding, ultrasonic welding, and the like. Where inner and outer liners are used, the ring frames may be sandwiched between the liners and held in place by attaching the liners to each other.

The prostheses 10 will typically have a length in the range from about 20 mm to 500 mm, preferably from 50 mm to 200 mm, with a relaxed diameter in the range from about 4 mm to 45 mm, preferably being in the range from about 5 mm to 38 mm.

Figure 2:
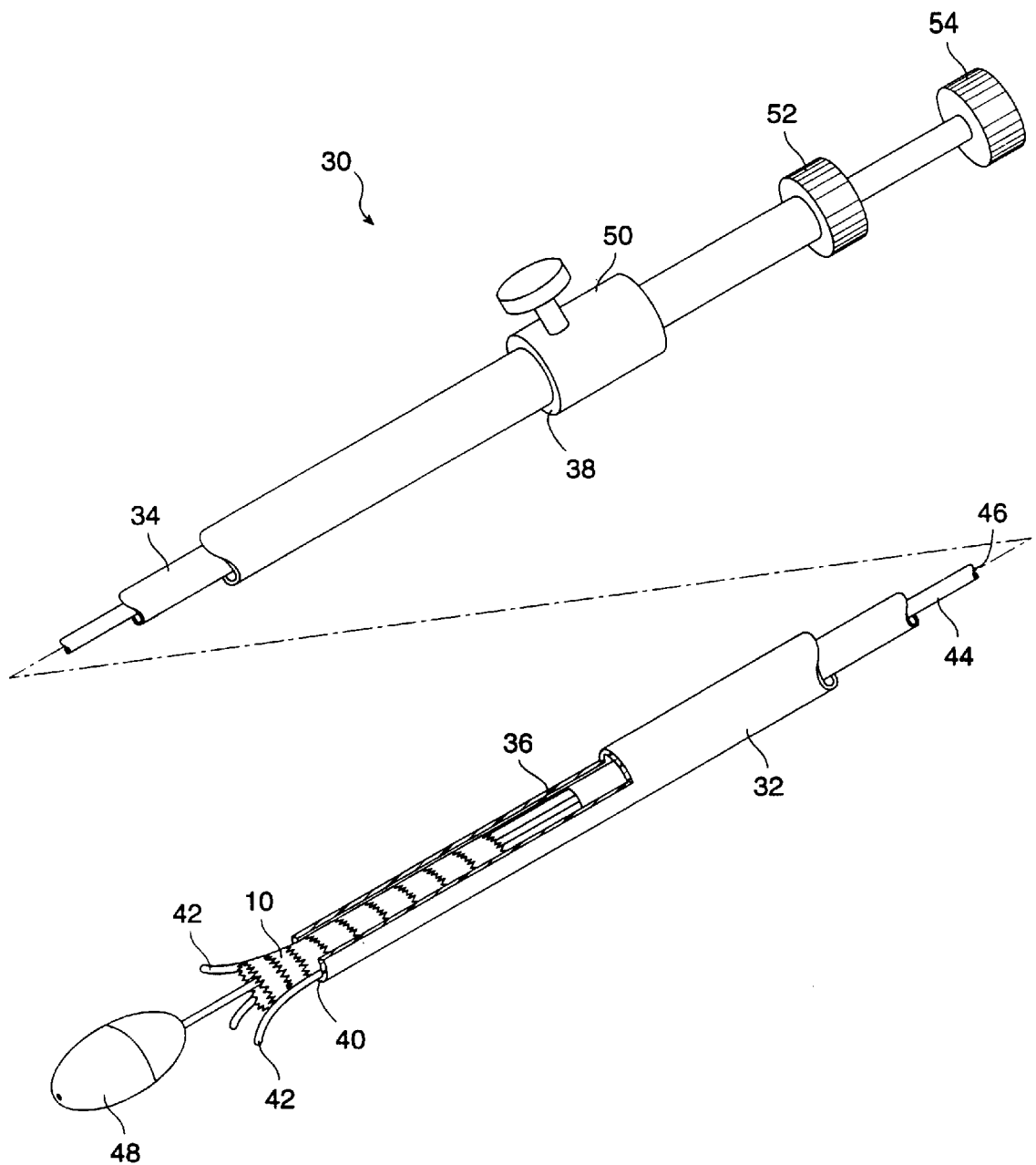
FIG. 2 is a perspective view of an exemplary delivery catheter for use with the prostheses of the present invention, with a portion of the distal end broken away to disclose a prostheses therein.

Referring now to FIG. 2, an exemplary delivery catheter 30 for use with the endoluminal prostheses of the present invention comprises a tubular cover 32 and a shaft 34. cover 32 has a central lumen 36 extending from a proximal end 38 to a distal end 40. Shaft 34 is slidably received within central lumen 36 and extends proximally of cover 32. A plurality of runners 42 extend distally from shaft 34. Runners 42 line a portion of the inner surface of lumen 36, and slide within the lumen of the shaft. Shaft 34 also has a lumen, in which a core shaft 44 is slidably disposed. Core shaft 44 has a guide wire lumen 46. Nosecone 48 is fixed to the distal end of core shaft 44, and can therefore be manipulated independently of runners 42.

Prostheses 10 is radially compressed and restrained within the plurality of runners 42. In turn, cover 32 prevents runners 42 from expanding outward. Runners 42 are formed from a hard material, and distribute the expansion load of prostheses 10 over the inner surface of central lumen 36. The deploying force is applied proximally against a slider 50 attached to a distal end 38 of cover 30, while holding a luer fitting 52 at the distal end of shaft 34, thereby withdrawing the cover proximally from over the prostheses. An additional luer adapter 54 at the distal end of core shaft 44 allows the core shaft to be manipulated independently, and to be releasibly secured to the shaft 34. Exemplary methods and devices for placement of the prostheses of the present invention are more fully described in co-pending U.S. patent application Ser. No. 08/475,200, filed Jun. 7, 1995, the full disclosure of which is incorporated herein by reference.

Figure 3:
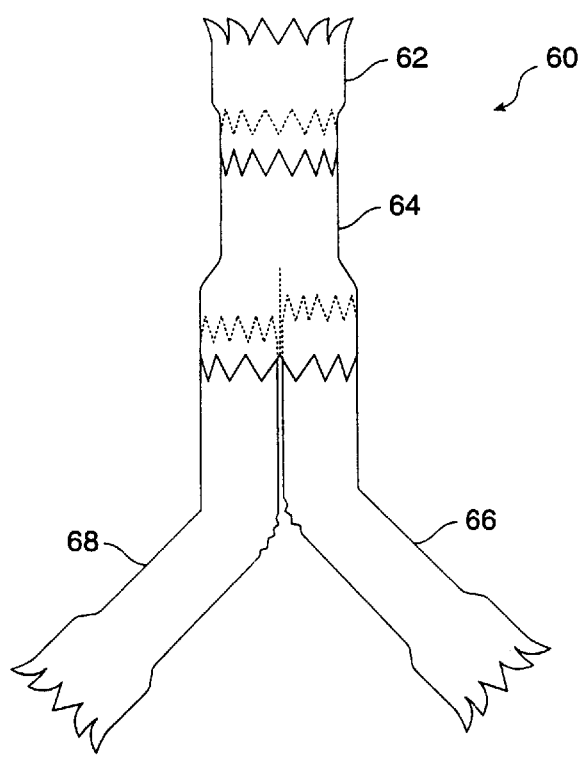
FIG. 3 illustrates a modular branching endoluminal prosthesis assembled from expansible prosthetic modules.

Although the structures and methods of the present invention will at times be described with reference to simple tubular prostheses having a single lumen, it should be understood that the present invention also generally encompasses more complex branching and modular endoluminal prostheses. Referring to FIG. 3, for example, a branching endoluminal stent-graft 60 is assembled from prosthetic modules selected to match the needs of the diseased vascular system of the patient. A common lumen cuffed prosthetic module 62 seals and anchors the assembled prosthesis in the body lumen, typically within the abdominal aorta below the renal arteries and above the left and right iliac arteries. Y-connector module 64 engages cuffed common lumen module 62, and separates the blood flow for the iliac arteries. First angled branching prosthetic module 66 and second angled branching prosthetic module 68 engage the branch lumens of Y-connector module 64 to direct the luminal flow along first and second branching body lumens.

The modular construction and expansible structure of branching prosthesis 60 allows individual tailoring of the common lumen, first branch lumen, and second branch lumen to match the geometry of the body lumen system. For example, a maximum perimeter of common lumen cuffed module 62 may be selected independently of the branching lumen perimeter limits. Additional sealing cuff structures and methods are described in co-pending U.S. patent application Ser. No. 08/525,989, filed Sep. 8, 1995, the full disclosure of which is also incorporated herein by reference.

Figure 4:
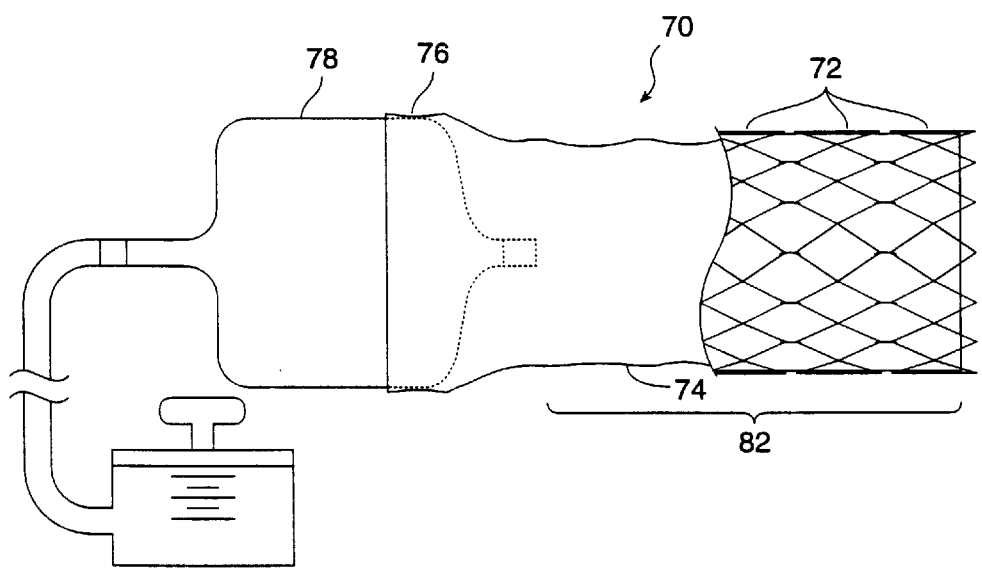
FIG. 4 is a schematic illustration of a method for selectively expanding an integral prosthetic sealing cuff.

The orientation indication markers of the prostheses of the present invention are particularly advantageous for use with the radially expansible prosthesis shown schematically in FIG. 4. An expansible prosthesis 70 has frame rings 72 sutured to an expansible liner 74. Expansible liner 74 is formed from a material which expands plastically when subjected to a stress beyond a yield strength, and which remains expanded when the stress is removed, ideally exhibiting little or no spring back. Suitable expansible liner materials include partially oriented polyester fibers, PTFE, or inexpansible fibers wrapped around an expansible fiber, a frangible fiber, or a dissolvable fiber, and the like. By subjecting a cuff 76 to the expansive force of balloon 78, the liner perimeter at a selected cross-section is increased. Advantageously, the expansion of expansible prosthesis 70 may be performed prior to shipping the prosthesis as a production step, at the surgical site prior to introduction of the prosthesis within the patient body, or preferably, after deployment of the prosthesis within a body lumen using an angioplasty-type balloon catheter or other minimally invasive expansion device.

Frame rings 72 of expansible prosthesis 70 may comprise a material which is resilient, malleable, or some combination of the two. When resilient, frame rings 72 will preferably be radially restrained by expansible liner 74, even after expansion of the liner to the predetermined limit. Such a liner-restrained stent-graft structure avoids any loosening of the liner after balloon 78 has been removed. As explained in co-pending U.S. patent application Ser. No. 08/595,944, filed Feb. 6, 1996, the full disclosure of which is also incorporated herein by reference, the cuff 76 of expansible prosthesis 70 often expands only to a predetermined limit, at which an element of either the liner 74 or the frame rings 72, or in some embodiments, the interface between the two, impedes further expansion.

Figure 5A:
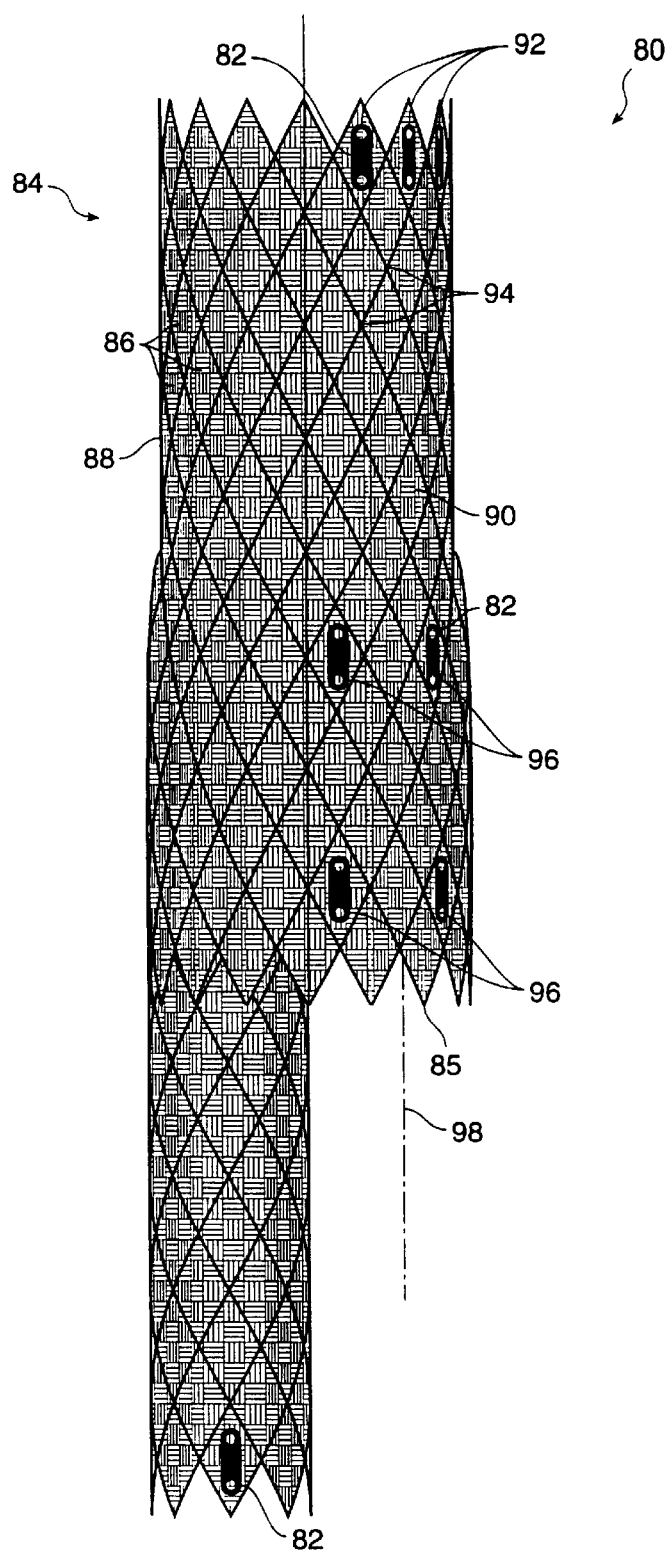
FIGS. 5A–C illustrate orientation indicating stent-grafts having a liner that supports marker elements, the marker elements comprising imagable bodies which define a pattern that facilitates orienting and assembling the prostheses in situ when the prosthesis is imaged fluoroscopically within a body lumen.

Referring now to FIG. 5A, an orientation indicating bifurcated prosthesis 80 includes a plurality of discrete marker elements 82 which form an orientation indicating pattern 84 when imaged using fluoroscopy, ultrasound, or other imaging modalities. Such bifurcated prostheses will be particularly useful for reinforcing abdominal aortic aneurysms which extend into one or both iliac arteries, and will typically be used in combination with a secondary prosthetic module engaging port 85 to seal the port to the body lumen system. Toward that end, pattern 86 preferably indicates the axial location of the ends, and the axial and radial orientation of port 85, when the prosthesis is in a radially compressed configuration within a delivery catheter, and after deployment to assist deploying the secondary prosthesis within port 85.

Minimizing the radial dimensions of the prosthesis significantly facilitates the intravascular maneuvering of the prosthesis during positioning and deployment. Therefore, it is generally desirable that marker elements 82 have the least possible volume to avoid increases in the delivery catheter cross-section. Furthermore, marker elements should not interfere with the radial expansion of the prosthesis from the radially compressed configuration to the radially expanded configuration, during which perforations 86 of frame 88 expand substantially. On the other hand, the pattern should provide a sharp image, despite the fact that frame 88 will often at least partially obscure the pattern when the prosthesis is imaged.

For the above reasons, marker elements 82 are preferably aligned with perforations 86, ideally being substantially disposed within the perforations to maximize their image contrast against the generally radiographically clear liner 90. Generally, supporting the marker elements with the liner, rather than attaching them directly to the frame, also helps avoid interference between the marker elements and the expansion of the surrounding frame structure.

Additionally, supporting the marker elements on the liner so that they are separated from the frame will help to avoid erosion of the frame, as the marker elements will not rub against the frame with physiological movement.

Pattern 84 defined by marker elements 82 includes several novel features. A port orientation indicator 92 is preferably disposed adjacent an end of the prosthesis which will be expanded before the port, and helps to verify that the orientation of port 85 will be aligned properly with the intended branching body lumen before the port is expanded in position. Fine rotational alignment of the prosthesis is facilitated by including roughly opposed marker elements 94, so that the preferred radial orientation of the prosthesis can be provided by orienting the imaging mechanism relative to the body lumen system surprisingly, in work done in connection with the present invention, such radial alignment has been found to be improved by axially offsetting opposed marker elements, so that the elements do not partially block each other's image during alignment, and to help distinguish a "front" marker element from a "back" marker element.

A still further feature of pattern 84 is the two axially separated gates 96 adjacent port 85. The axial positions and separation of these gates gives a visual indicator of the allowable prosthetic module overlap when the prosthesis is deployed and imaged in situ. Modular prostheses having less than a predetermined overlap may not be adequately fixed together, while branches which extend too far into the bifurcated prosthesis may lead to imbalanced flow between the branches, or may even fold over and substantially block the lumenal flow to one or both branches.

Generally, an overlap is acceptable when an end (or an associated overlap marker) of a secondary prosthesis is disposed between the gates. Advantageously, the gates are defined by markers on either side of the port centerline, greatly improving the visibility of the markers when the delivery catheter of a secondary prosthesis enters the port. Furthermore, a pattern including such gates provides a clear demarkation of the target path between the markers when advancing a guidewire and/or a delivery catheter into the port 85 of bifurcated prosthesis 80.

Figure 5B:
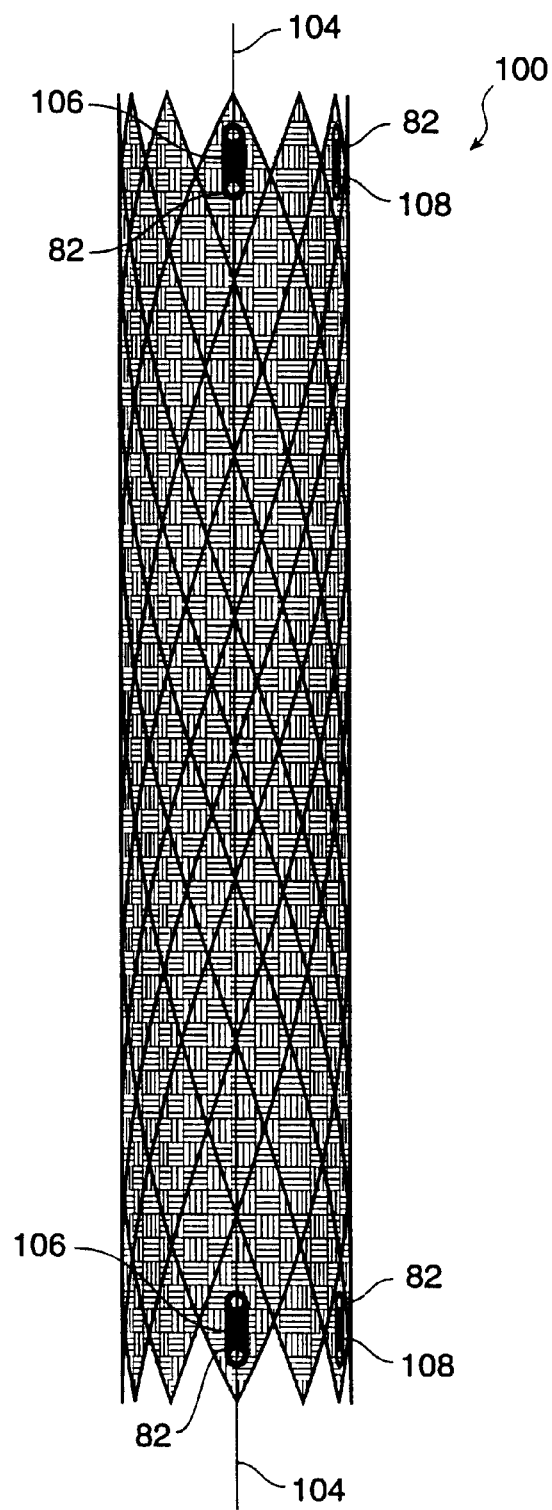
Figure 5C:
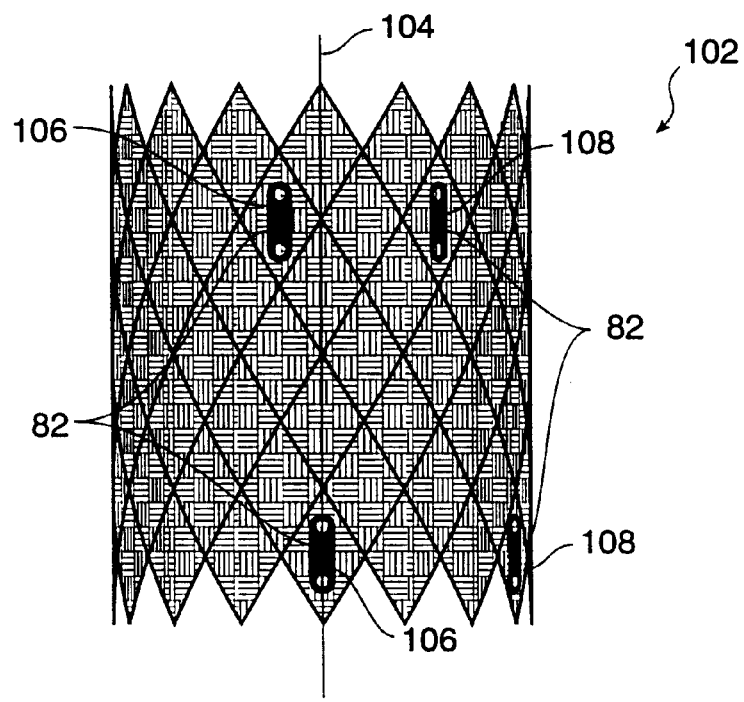

Referring now to FIGS. 5B and C, branch secondary prosthetic module 100 and trunk secondary prosthetic module 102 also include image markers 82 which define patterns to facilitate axially positioning and radially orienting these modules within a body lumen, particularly with reference to bifurcated prosthesis 80 described above.

Each of branch module 100 and trunk module 102 include marker elements 106 which produce an image which is aligned along a prosthetic centerline 104 when the prosthesis is properly positioned relative to the imaging apparatus. Advantageously, such a marker element may be aligned with a guidewire passing through the prosthetic lumen even if no other rotational alignment marker is provided, thereby minimizing the total number of markers. Asymmetric marker elements 108 are radially offset from the centerline markers, preferably defining a radial angle between about 15° and 70° with centerline markers 106, to ensure that the modules are not 180° out of rotational alignment, which could be problematic if the modules have a preferred bend angle or some other asymmetric structure. A roughly 30° radial angle is preferred, as flat thin marker elements will produce smaller images when viewed edge-on that tend to blend into the frame as the angle approaches 90°, while smaller angles will be difficult to differentiate. Furthermore, such significantly off-centerline markers are less likely to be overshadowed by subsequent guidewire or delivery catheter placements. Left and right off-centerline markers may be included to ensure the prosthesis is not roughly 150° out of rotational alignment. The asymmetric marker elements can also easily be aligned with the port indicator markers 92 or otherwise consistently aligned with some other imagable structure of the bifurcated prosthesis of FIG. 5A.

Figure 6:
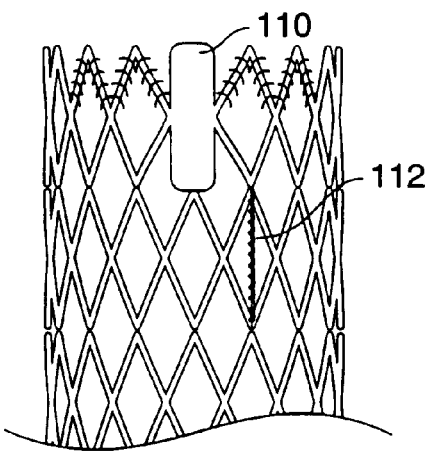
FIG. 6 illustrates an endoluminal stent-graft having an alternative orientation indicating marker element structure formed integrally with the frame, according to the principles of the present invention.

Referring now to FIG. 6, one optional structure for the marker element comprises an integral frame marker 110 formed by locally varying the perforation pattern of the frame. The frame marker 110 is generally wider than the surrounding frame structure, and will therefore provide an identifiable marker. As the frame material will generally be selected for strength rather than imaging contrast (often comprising a high strength biocompatible alloy such as stainless steel, a shape memory alloy such as Nitinol™, or the like), such an integral marker may only provide a moderate image under fluoroscopy. Conveniently, the image contrast of such an integral marker element may be improved by selectively thickening, or by coating integral frame marker 110 with a high contrast material, such as gold, platinum, tantalum, or the like.

Regardless of the specific radiopaque marker structure selected, the prostheses of the present invention will often include different materials for the frame and for the marker elements. As described above, the frame material will often comprise a high strength metal, while the marker elements will generally comprise a radiopaque metal or a metal which produces an enhanced ultrasound image. One potential problem with known endoluminal prostheses having such dissimilar metals is that a substantial difference in Electromotive Force (EMF) of adjacent metallic materials may promote corrosion. To avoid this problem, the present invention provides endoluminal prostheses with frames and marker element having similar EMF characteristics. A particularly preferred combination combines frames which include Nitinol and marker elements which include tantalum. These materials exhibit excellent strength and imagability, respectively, and are of sufficiently similar characteristics to avoid electrolytic corrosion.

An alternative frame supported marker element, perforation cross-member 112, is also illustrated in FIG. 6. This structure will also attach directly to the frame, but will generally have a coiled or otherwise deformable structure to accommodate the changes in perforation size during deployment. Unfortunately, such frame supported marker elements will tend to interfere to some extent with the radial expansibility of the frame.

Figure 7:
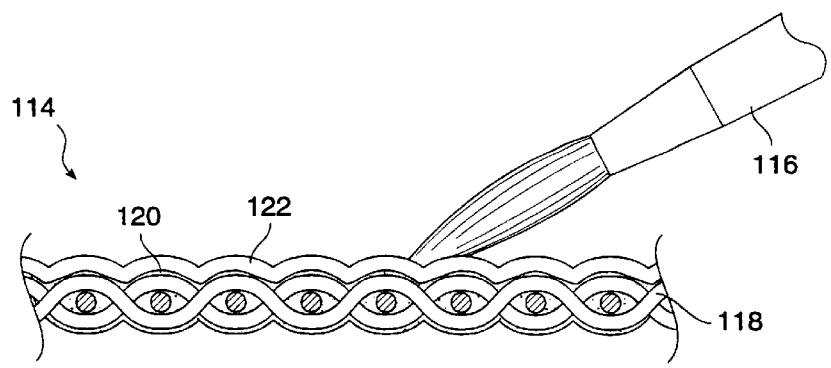
FIG. 7 illustrates a method for applying a radiopaque marker element to a polyester liner of an endoluminal stent-graft by painting the liner with a radiopaque compound and covering the marker with an overcoat.

To avoid marker elements which displace or otherwise interfere with the expansible frame structure, the present invention also provides radiopaque ink marker elements 114 as illustrated in FIG. 7. Such markers may be applied to a polyester fabric liner 118 with a small caliber paintbrush 116, by silkscreening, or the like, and will generally be applied as a radiopaque compound comprising radiopaque particles in a polyester matrix which is dissolved in a polyester solvent. The radiopaque compound 120 will wick through and bond permanently to the liner, while an overcoat 122 (applied as a solution comprising a polyester matrix in a polyester solvent) will help avoid flaking of the dried compound.

Preferably, the radiopaque particles comprise tantalum, the particles ideally being between about 1 and 5 microns, and are continuously blended with the compound before application to the liner. A suitable polyester matrix may comprise a polyester such as Dacron™, while the solvent may include hexofluoro 2-propanol, methylene chloride, a combination of both, or the like. In some embodiments, it may be advantageous to pre-wet the polyester liner prior to applying the compound with a polyester solvent, typically comprising a diluted version of the solvent used in the radiopaque compound.

Figure 8:
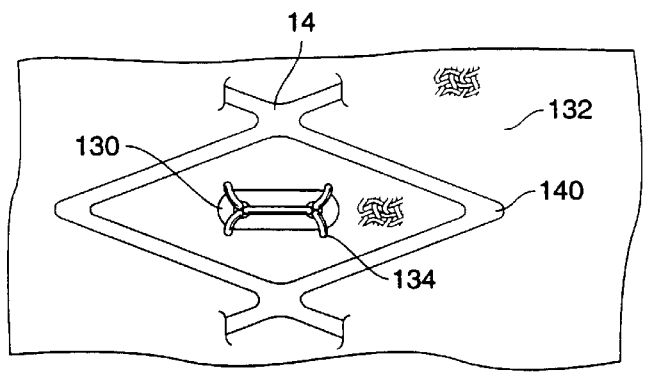
FIGS. 8–8C illustrate a preferred radiopaque marker element comprising an imagable body in the form of a plate having a passage to facilitate attachment of the plate to the liner.
Figure 8A:
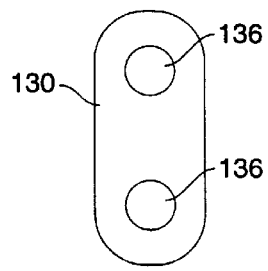
Figure 8B:
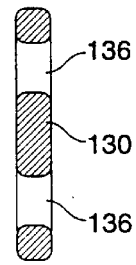
Figure 8A:
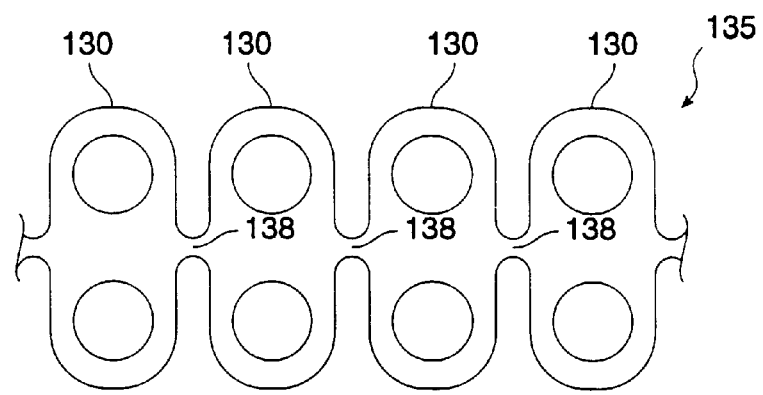

A preferred marker element structure comprising an imagable body attached to the liner will be described with reference to FIGS. 8–8C. The imagable body here comprises a plate 130 stitched to liner 132 with sutures 134. Plate 130 includes two passages 136 to facilitate attachment, and will generally comprise a material which provides a high contrast when imaged, typically including a radiopaque material such as gold, platinum, or other implantable metals. Ideally, plate 130 comprises tantalum having a thickness of at least about 0.002 inches, preferably being about 0.01 inches. Such tantalum plates may be mass produced by die cutting or laser cutting sheet stock, preferably leaving a chain of plates 135 attached by detachable tabs 138 and ready for use. In most embodiments, the edges of plates 130 will be rounded to avoid any injury to adjacent tissues, and to avoid cutting any liner or attachment fibers.

The plates will often be sewn to the outer surface of the liner material to avoid interference with the vascular flow or the generation of thrombus. Advantageously, where the liner is also supported by an external frame 140, the prosthetic lumen remains uninterrupted. Furthermore, where the plates are generally attached along a radius of the liner, they should not substantially interfere with expansion of the liner material. Optionally, expansible sutures (such as a partially oriented polyester yarn) may be used to attach the plates.

The imagable bodies of the present invention could comprise a variety of alternative shapes and liner attachment mechanisms. Snaps, rivets, staples, and the like could attach through the liner, or knobs or other shapes could be sewn, adhesively bonded, or otherwise affixed to the liner within the scope of the present invention. Plates 130 having at least one passage 136 are generally preferred, however, as they provide a relatively large image, do not substantially distort or interrupt the prosthetic lumen, and can be very securely attached to the liner.

Figure 9:
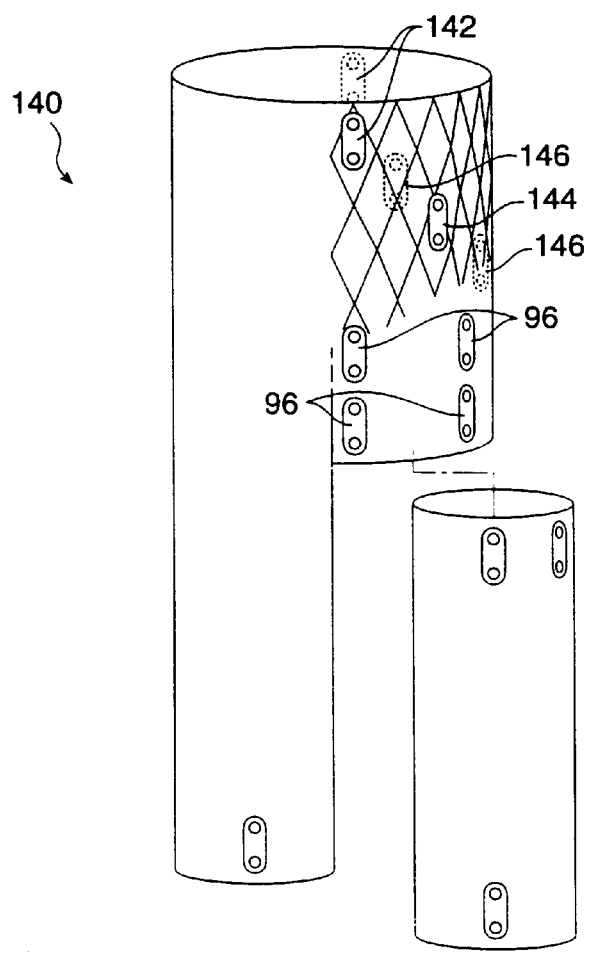
FIG. 9 illustrates an alternative pattern of radiopaque marker elements to facilitate orientation and assembly of an endoluminal prosthesis.

An alternative orientation indicating pattern is illustrated in FIG. 9, the pattern including opposed marker elements 142 which axially overlap when the prosthesis is rotationally aligned relative to the imaging system. Additionally, the port orientation is here indicated by alternating front port orientation markers 144 and rear port orientation markers 146. When these alternating port markers are lined up and evenly spaced, the prosthesis is aligned and the port is on the side of the prosthesis toward which the line of port orientation markers slant.

Figure 10A:
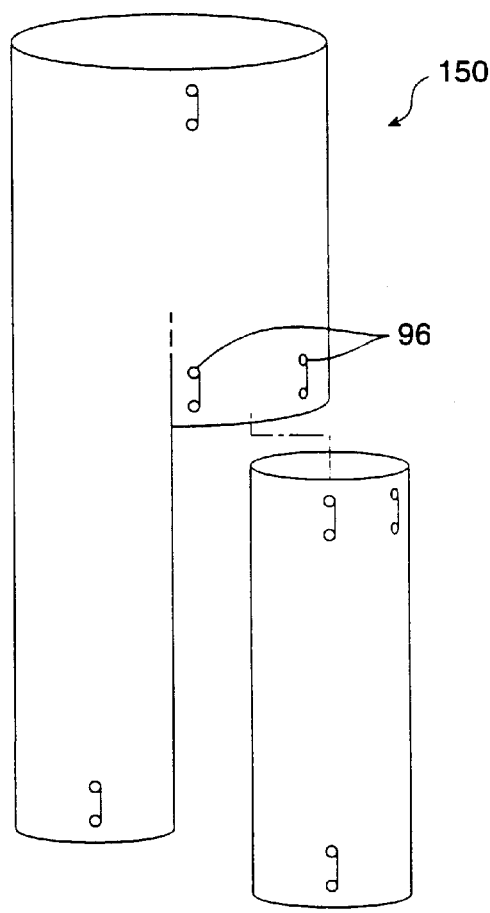
FIGS. 10A and B illustrate a still further alternative pattern of marker elements comprising wires having loops to facilitate stitching the marker elements to the liner.
Figure 10B:
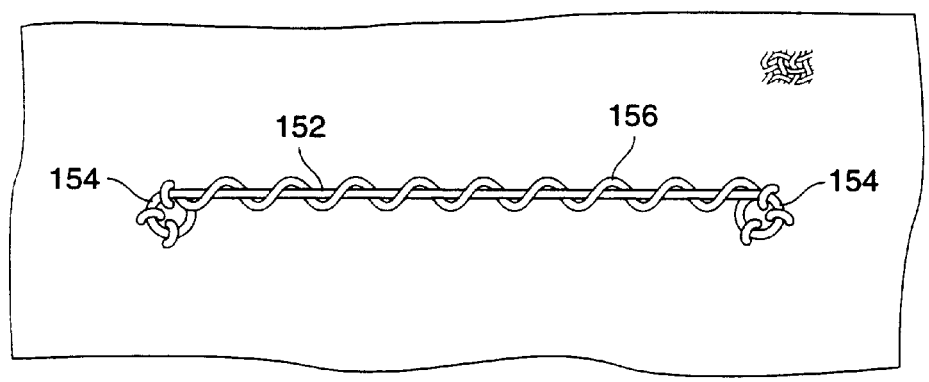

A still further marker element and pattern are illustrated in FIGS. 10A and B. Pattern 150 is defined by the images of wires 152 having loops 154 for attachment to the liner. Optionally, the contrast of the wires may be enhanced by windings 156, the wires and windings comprising a high contrast material, often including gold, platinum, tantalum, or the like. Advantageously, a single gate 96 formed with such wire marker elements may indicate an axial overlap range by careful selection of the length of the wires.

Figure 11:
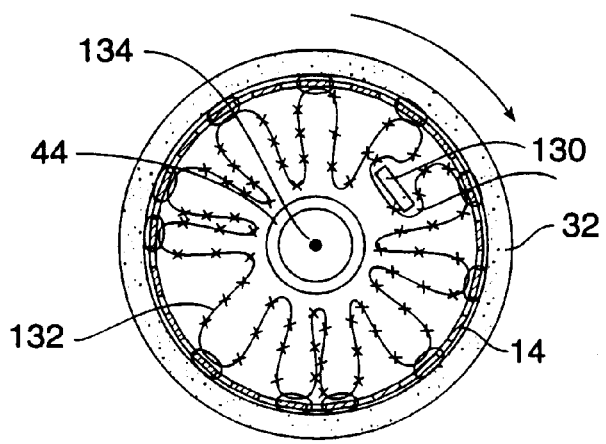
FIG. 11 illustrates an orientation indicating endoluminal prosthesis in small diameter configuration disposed within a delivery catheter, and shows a liner supported marker element which does not interfere with the expansion or compression of the prosthesis.

Referring now to FIG. 11, one advantage of the liner supported marker elements of the present invention is that the marker element can fold out of the way of the frame with the liner. Ring frame 14 can be tightly compressed within sheath 32, leaving little space between the frame arms.

Figure 12:
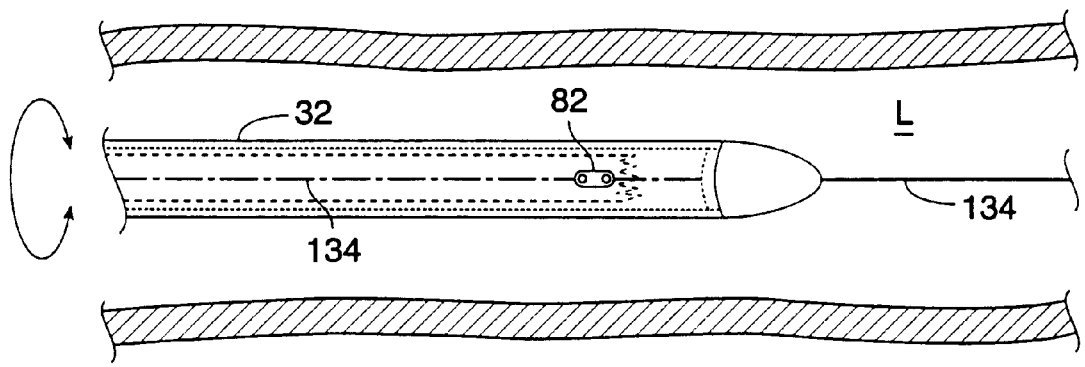
FIG. 12 illustrates a method for radially orienting an endoluminal prosthesis by aligning a marker element of the prosthesis with a guidewire passing through the prosthesis while the prosthesis is disposed within the delivery catheter.

Referring now to both FIGS. 11 and 12, a guidewire 134 may be used to radially align a prosthesis prior to deployment by rotating the catheter within a body lumen L to align an image of the guidewire with an image of a marker element. Hence, only a single marker element may be required for radial orientation.

Figure 13A:
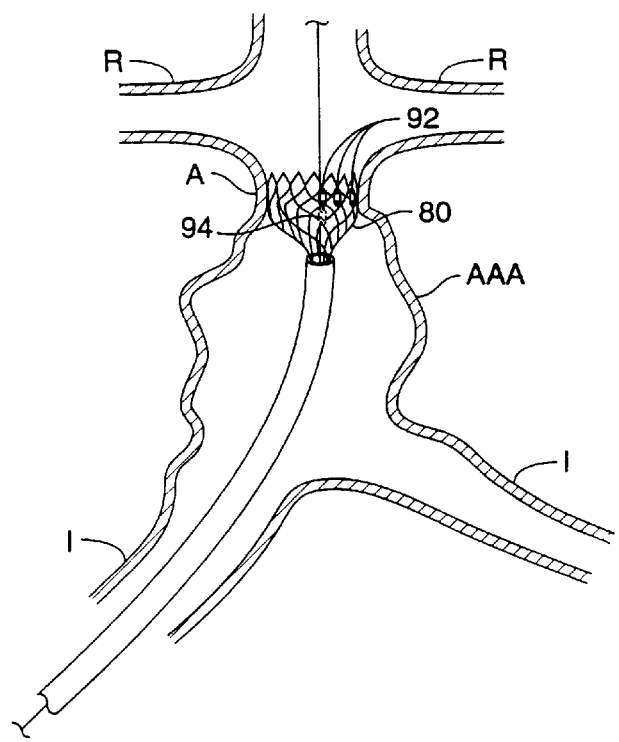
FIGS. 13A and B illustrate a method for deploying a bifurcating prosthesis which includes verifying the orientation of a branch port with port orientation indicating markers while the branch port remains compressed within the delivery catheter, and by advancing a secondary prosthesis through a gate at the expanded port, the gate defined by marker elements on either side of the port centerline.
Figure 13B:
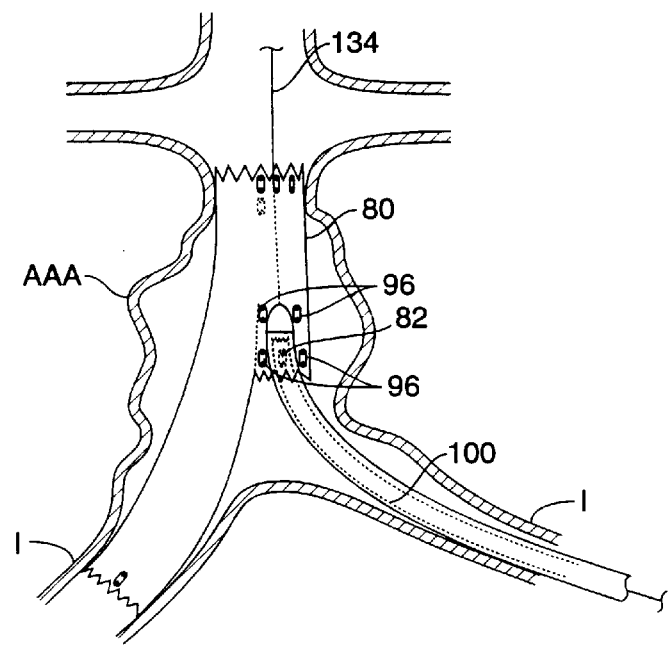

A method of deploying branching prosthesis 80 and branch module 100 for treatment of an abdominal aortic aneurysm AAA is illustrated in FIGS. 13A and B. Aneurysm AAA extends along the aortic artery A from below the renal arteries R and onto the iliacs I. The imaging system is typically oriented toward the plane of the aorta/iliac bifurcation. The catheter is introduced and axially positioned under fluoroscopy so that the prosthesis extends along the weakened aorta and into one of the iliacs. By rotating the catheter until the port indicator marker elements 92 are generally on the side of the opposite iliac, the port can be generally oriented to accept branch module 100. Further alignment can be provided by aligning axially offset opposed markers 94.

Once the prosthesis appears to be properly positioned and aligned, the distal end of the prosthesis is deployed. Advantageously, this provides a clear view of port orientation indicating marker elements 92 well before the port itself is expanded. If further rotational adjustment is necessary, it may be possibly to simply rotate the expanded prosthesis end against the healthy tissue beyond the aneurysm. Alternatively, the expanded end may be withdrawn into the catheter and repositioned or replaced much easier than if the sheath is withdrawn beyond the port itself. Clearly, if a superior approach is used, the port orientation indicating markers may instead be disposed adjacent the prosthetic branch end within the iliac to provide similar benefits.

The gates 96 adjacent the port on prosthesis 80 clearly indicate the path of the port axis to facilitate introduction of guidewire 134 and the delivery catheter for the branch module. Advantageously, the marker elements which define the gate can remain visible even when the delivery catheter is disposed in the port. This significantly eases positioning marker elements 82 adjacent the end of the branch module axially between gates 96, thereby assuring that the prosthetic overlap is within the predetermined allowable range.

Figure 14A:
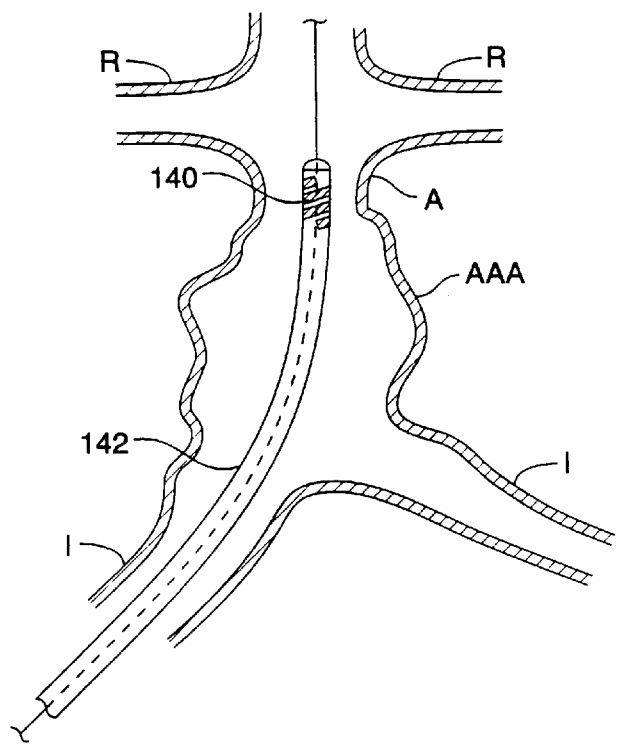
FIGS. 14A and B illustrate a method for deploying an endoluminal prosthesis by first placing a marker band, and by then deploying an end of the prosthesis adjacent the marker band.
Figure 14B:
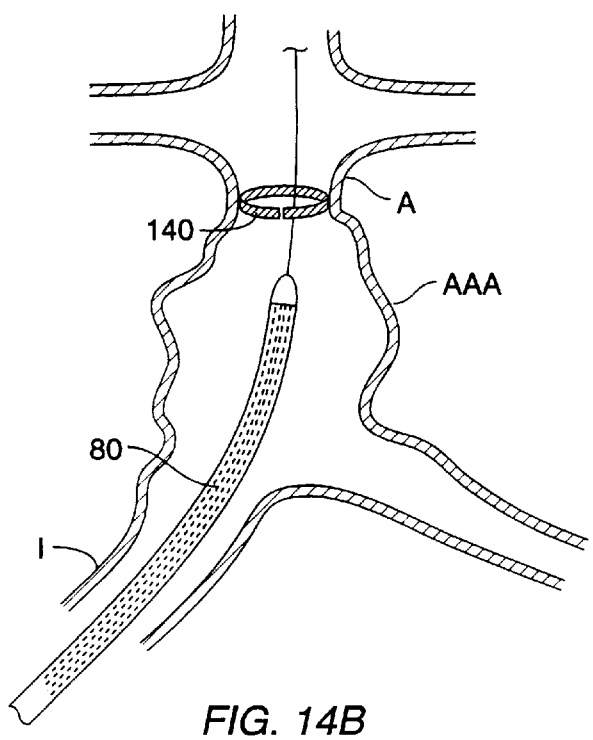
Figure 15:
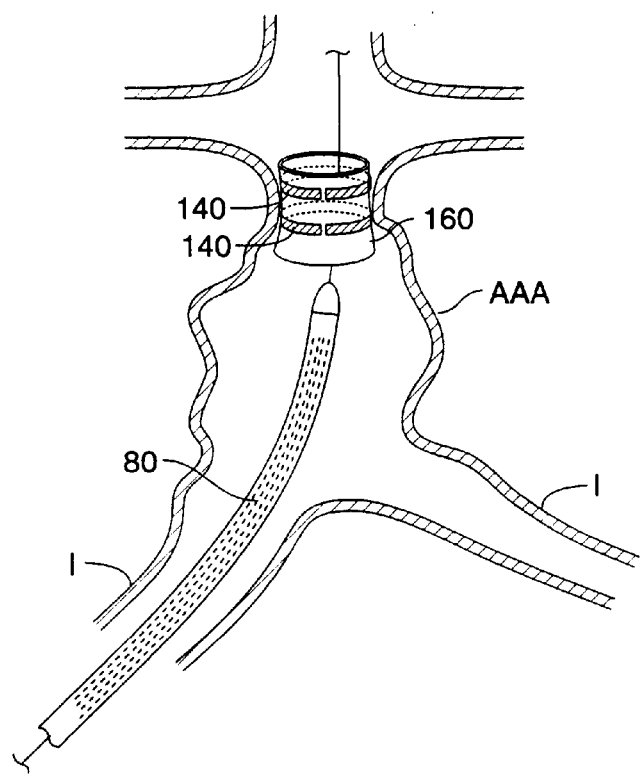
FIG. 15 illustrates a method for deploying an endoluminal prosthesis similar to the method illustrated in FIGS. 14A and B, in which a conformal sponge-like sealing gasket is deployed with two marker bands to clearly mark a target region and to seal between the end of the prosthesis and an irregular surrounding body lumen.
Figure 16A:
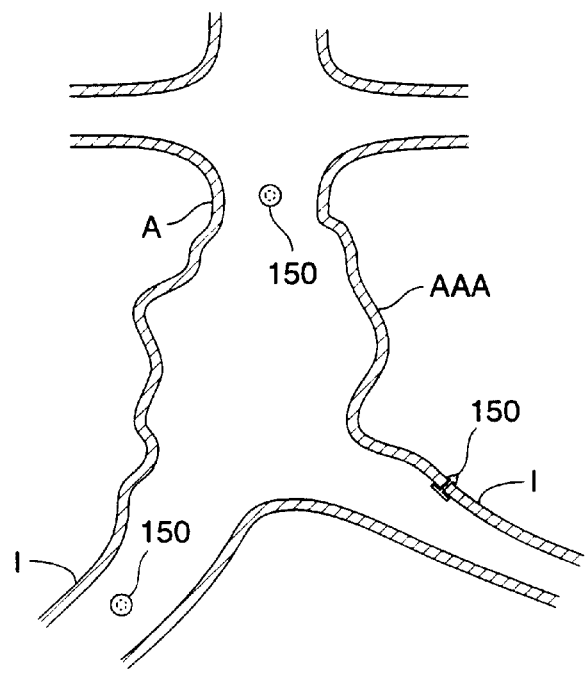
FIGS. 16A–D illustrate barbed endoluminal imagable bodies and a method for their use to mark the target location for an endoluminal prosthesis, according to the principles of the present invention.
Figure 16B:
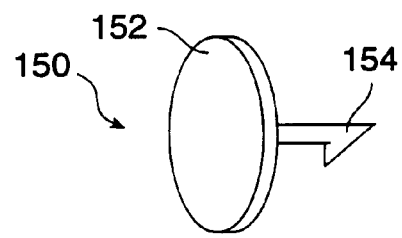
Figure 16C:
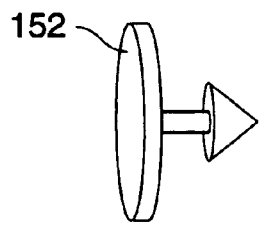
Figure 16D:
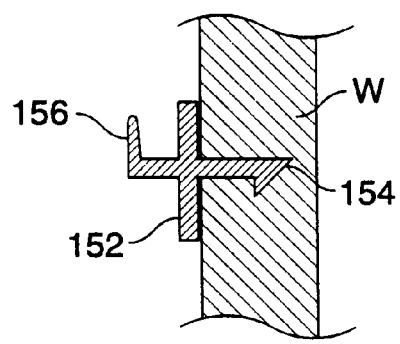

Methods and devices for providing target location markers with a body lumen, generally for use prior to deploying and endoluminal prosthesis, are shown in FIGS. 14A through 16D. Referring first to FIGS. 14A and B, a body lumen marker comprising a helical marker band 140 may be deployed with a catheter 142 to mark the specific target location for an end of the branching prosthesis 80. Advantageously, the marker band delivery catheter 142 may incorporate intravascular ultrasound (IVUS) imaging capabilities to more accurately determine the extent of aneurysm AAA than is possible using fluoroscopy alone. The deployed marker band 140 thereafter clearly marks the location for a subsequent fluoroscopically directed endoluminal prosthesis deployment (as shown in FIG. 14B), the marker band generally comprising a radiopaque material. optionally, a sealing gasket material is deployed with marker band 140 to seal between the later-deployed prosthesis and the surrounding body lumen, as shown in FIG. 15. Such a sealing gasket preferably comprises a sponge-like silicone or other polymer, as more fully explained in co-pending U.S. patent application Ser. No. 08/525,989, previously incorporated by reference. Additionally, two or more marker bands 140 may be deployed with each gasket to indicate a range of allowable axial positions, and optionally to help affix the gasket in position. Such marked sealing gaskets may be provided at each end of the prosthesis to fully seal the prosthetic lumen to the body lumen system. Marker bands 140 may comprise resilient or plastically expansible materials, but will preferably have an axial length of less than about 2 cm, ideally less than about 1 cm, to accurately mark a specific axial position.

Alternative endoluminal body lumen markers are illustrated in FIGS. 16A–D. Generally, these endoluminal markers 150 comprise imagable bodies 152 which are held in position by barbed protrusions 154 which penetrate at least partially into the lumenal wall W. Advantageously, the tubular endoluminal prosthesis may be positioned over the body lumen markers, thereby helping to hold them in position against the body lumen wall. In some embodiments, the body lumen markers may include hooks 156 or other prosthesis engaging structures opposite the barbed protrusion 154 to maintain the position of the subsequently deployed prosthesis within the body lumen. The body lumen markers will typically comprise a radiographic material such as tantalum, gold, platinum, or the like, and may be deployed using a high torque, high control delivery catheter, a balloon catheter, or the like.

Although the exemplary embodiments have been described in some detail, by way of illustration and example, the scope of the present invention is limited solely by the appended claims.

The marker bands 140 and endoluminal markers 150 may also find use in measuring or verifying the actual diameter of the vessel prior to prosthesis. Such independent marker elements which engage the lumenal wall will also be useful in follow-up procedures to determine whether the prosthesis has migrated, whether there has been any change in length or diameter of the aneurysm or the prosthesis over time.

What is claimed is:

1. An endoluminal prosthesis for deployment in a body lumen of a patient body, the prosthesis comprising:
   a tubular fabric liner having a proximal end, a distal end, and a lumen therebetween;
   a radially expandable frame supporting the liner; and
   a plurality of radiopaque marker elements, each marker element comprising a plate having at least one passage therethrough and stitched through the passage to the liner, the marker elements indicating a position of the prosthesis when the prosthesis is imaged within the body lumen, wherein the marker elements are not directly attached to the frame.

2. A prosthesis as in claim 1, wherein the marker elements are not in contact with the frame when the frame is radially expanded.

3. A prosthesis as in claim 1, wherein the plates comprise a material selected from the group consisting of tantalum, platinum, and gold.

4. An endoluminal prosthesis for deployment in a body lumen of a patient body, the prosthesis comprising:
   a radially expandable tubular body having a proximal port, a distal port, and a lumen therebetween, the lumen defining a centerline; and
   a plurality of marker elements which define a pattern when the prosthesis is imaged within the patient body, wherein each marker element comprises a high contrast plate and the pattern includes a gate disposed adjacent to the distal or proximal port, the gate comprising radially separated marker elements on opposed sides of the centerline when the prosthesis is properly orientated so as to facilitate deployment of a secondary prosthetic module within the adjacent port of the prosthesis.

5. A prosthesis as claimed in claim 4, wherein the pattern includes two axially separated gates defining an allowable prosthetic overlap region therebetween.

6. A prosthesis as claimed in claim 4, wherein the pattern includes at least one marker element that is rotatably alignable with the centerline within the body lumen.

7. A prosthesis as claimed in claim 6, wherein the pattern includes two marker elements which are roughly radially opposed relative to the centerline, wherein the two marker elements are axially offset.

8. A prosthesis as claimed in claim 4, wherein the prosthesis comprises a bifurcated tubular body having a trunk portion, a first branch portion, and a branch port for receiving a second branch portion, and wherein the pattern includes at least one marker element adjacent the distal end of the prosthesis which indicates the orientation of the branch port before deployment of the branch port.

9. An endoluminal body lumen marker for use in positioning a later deployed endoluminal prosthesis in a body lumen of a patient high contrast plate, the lumen marker comprising a body which produces a sharp contrast when imaged within the body lumen, and a support structure which maintains a position of the lumen marker within the body lumen until the prosthesis is positioned and deployed across the lumen marker.

10. A body lumen marker as claimed in claim 9, wherein the support structure comprises a barbed protrusion for attaching the plate to the lumenal wall.

11. A body lumen marker as claimed in claim 9, wherein the deployed marker has an axial length of less than about 2 cm.

12. A body lumen marker as claimed in claim 9, wherein the support structure comprises a radially expandable radiopaque band which engages the surrounding body lumen and which marks an axial target location for an end of the prosthesis.

13. A body lumen marker as claimed in claim 12, wherein the band comprises a helical coil before radial expansion.

14. A body lumen marker as claimed in claim 12, further comprising a conformable tubular gasket which expands with the band and which seals between the prosthesis and the surrounding body lumen when an end of the prosthesis is deployed within the axial target location.

15. A body lumen marker as claimed in claim 14, further comprising a hook extending from the imagable body roughly opposite the barbed protrusion to anchor the prosthesis deployed over the imagable body.

16. An endoluminal stent-graft comprising:
a tubular liner having a lumen which defines an axis; and
a tubular frame supporting the liner, the frame having a plurality of marker elements integrally formed with the tubular Frame, the marker elements defining a pattern which indicates a position of the prosthesis when the prosthesis is imaged within the body lumen.

17. A stent-graft as claimed in claim 16, wherein the frame comprises a radiopaque material, and wherein the marker elements comprise portions that are wider than adjacent expandable structural elements of the frame to provide an enhanced radiographic contrast.

18. A method for assembling an endoluminal prosthesis at a target location of a body lumen, the method comprising:
introducing a first tubular endoluminal prosthetic module into the body lumen;
positioning the first module adjacent to the target location;
radially expanding the first module to deploy the module adjacent to the target location, the expanded first module having first and second marker elements disposed adjacent to a port, wherein each marker element comprises a high contrast plate;
introducing a second tubular prosthetic module into the body lumen; and
positioning the second module within the port of the first module by imaging the first module and axially advancing the second module between the first and second marker elements.

19. A method as claimed in claim 18, wherein the second module positioning step further comprises axially advancing the second module within the port beyond the first and second marker elements while the images of the first and second marker elements are visible on opposite sides of the second module.

20. A method as claimed in claim 19, wherein the second module positioning step further comprises axially positioning an element of the second module within the port between an axial position of the first and second marker elements and an axial position of third and forth marker elements of the first module.

21. A method for positioning a tubular endoluminal prosthesis at a target location of a body lumen, the method comprising:

introducing a guidewire through the body lumen and advancing the guidewire beyond the target location;
advancing the prosthesis over the guidewire so that the guidewire passes through a lumen of the prosthesis;
radially orienting the prosthesis by imaging the prosthesis within the body lumen and aligning an image of a marker element of the prosthesis with an image of the guidewire, wherein, the marker element comprises a high contrast plate.

22. A method for positioning a tubular endoluminal prosthesis at a target location of a body lumen, the method comprising:
introducing the prosthesis into the body lumen;
positioning the prosthesis adjacent to the target location;
radially orienting the prosthesis by imaging the prosthesis within the body lumen and aligning an image of a first marker element of the prosthesis with an image of a second marker element of the prosthesis, wherein the first and second marker elements each comprise a high contrast plate and are axially offset from each other.

23. A method for verifying the radial orientation of a port of a branching tubular endoluminal prosthesis within a body lumen, the method comprising:
introducing the prosthesis into the body lumen;
radially orienting the prosthesis;
deploying an end of the prosthesis which is separated from the port by axially withdrawing a surrounding sheath and allowing the prosthesis end to expand resiliently; and
imaging at least one port orientation indicating marker element disposed on the expanded end of the prosthesis while the prosthesis adjacent the port remains compressed, wherein the marker element comprises a high contrast plate.

24. A method for deploying an endoluminal prosthesis, the method comprising:
introducing a marker element into a body lumen and deploying the marker element so as to mark a target location of the body lumen;
introducing the prosthesis into the body lumen;
aligning the prosthesis with the deployed marker element; and
deploying the aligned prosthesis within the body lumen.

25. A method as claimed in claim 24, further comprising imaging the marker element and prosthesis in the body lumen to determine changes in their relative positions.

26. An endoluminal prosthesis comprising:
a frame comprising a high-strength material; and
a marker element comprising a high-contrast imagable material
wherein the high-strength and high-contrast materials have similar electromotive force characteristics to avoid corrosion.

27. A prosthesis as claimed in claim 26, wherein the high-strength material comprises a shape memory alloy, and wherein the high-contrast material comprises tantalum.

* * * * *